United States Patent
Bal-Tembe et al.

(10) Patent No.: US 8,263,587 B2
(45) Date of Patent: Sep. 11, 2012

(54) BENZOXAZEPINE COMPOUNDS, THEIR PREPARATION AND USE

(75) Inventors: Swati Bal-Tembe, Maharashtra (IN); Bansi Lal, Maharashtra (IN); Satish Namdeo Sawant, Maharashtra (IN); Anagha Suhas Kulkarni, Maharashtra (IN)

(73) Assignee: Piramal Healthcare Limited, Mumbai (IN)

( * ) Notice: Subject to any disclaimer, the term of this patent is extended or adjusted under 35 U.S.C. 154(b) by 390 days.

(21) Appl. No.: 12/447,809

(22) PCT Filed: Nov. 1, 2007

(86) PCT No.: PCT/IB2007/054431
§ 371 (c)(1),
(2), (4) Date: Apr. 29, 2009

(87) PCT Pub. No.: WO2008/053446
PCT Pub. Date: May 8, 2008

(65) Prior Publication Data
US 2011/0152247 A1    Jun. 23, 2011

Related U.S. Application Data

(60) Provisional application No. 60/856,138, filed on Nov. 2, 2006.

(51) Int. Cl.
*A01N 43/00* (2006.01)
*A61K 31/553* (2006.01)
*A61K 31/554* (2006.01)

(52) U.S. Cl. .................. 514/211.09; 540/552
(58) Field of Classification Search ............. 514/211.09; 540/552
See application file for complete search history.

(56) References Cited

U.S. PATENT DOCUMENTS

| 6,489,322 B1 | 12/2002 | Macdonald et al. | |
|---|---|---|---|
| 6,534,496 B1 * | 3/2003 | Ishihara et al. | 514/212.07 |
| 2006/0173183 A1 | 8/2006 | Powers et al. | |

FOREIGN PATENT DOCUMENTS

WO    WO 02/051838    7/2002

OTHER PUBLICATIONS

Vippagunta, et al. Advanced Drug Delivery Reviews, 48, 2001, p. 18).*
Target et al "Synthetic inhibitors of interleukin-6 II: 3,5-diaryl pyridines and meta-terphenyls", Biorganic & Medicinal Chemistry Letters, vol. 5, No. 18, pp. 2143-2146, 1995.*
Fabian et al "Azabenzenes (Azines)—The nitrogen derivatives of benzene with one to six N atoms: stability, homodesmotic stabilization energy, electron distribution, and magnetic ring current; a computational study", Can. J. Chem. vol. 82, pp. 50-69, 2004.*
Niseen et al "Effect of Rosiglitazone on the Risk of Myocardial Infarction and Death from Cardiovascular causes", The New England Journal of Medicine, Jun. 14, 2007, vol. 356, No. 24, pp. 2457-2471.*
Schafer et al. Drug Discovery Today 2008, 13 (21/22), 913-916.*
Horig et al. Journal of Translational Medicine 2004, 2(44).*
Wolff Burger's Medicinal Chemistry and Drug Discovery, Fifth Edition, vol. I: Principles and Practice, Wiley-Interscience 1995, pp. 975-977.*
Cantello, B. C. C., et al. "[[107 -(Heteroeyelylamino) alkoxy] benzyl]-2,4-thiazolidinediones as Potent Antihyperglycemic Agents." *Journal of Medicinal Chemistry* (1994) vol. 37, No. 23, pp. 3977-3985.
Vassault, Anne "2 Oxidoreductases: Dehydrogenases Acting on CHOH Groups" *Method in Enzyme Analysis* (1984) vol. 3 pp. 118-125.
Murakami, K, et al. "A Novel Insulin Sensitizer Acts a a Coligand for Peroxisome ProliferatorActivated Receptor a(PPAR-α) and PPAR-γ" *Diabetes* (1998) vol. 47, pp. 1841-1847.
Gebhardt, R., et al. "Biliary Secretion of Soduim Fluorescein in Primary Monolayer Cultures of Adult Rat Hepatocytes and its Stimulation by Nicotinamide" *Journal of Cellular Science* (1982) vol. 56 pp. 233-244.
Willson T.,et al. "The PPARs": From Orphan Receptors to Drug Discovery *Journal of Medicinal Chemistry* (2000) vol. 43(4), pp. 527-550.
Lehmann, J. et al. "An Antidiabetic Thiazolidinedione Is a High Affinity Ligand for Peroxisome Proliferator-activated Receptor γ (PPAR-γ)*" *Journal of Biological Chemistry* (1995) vol. 270 pp. 12953-12956.

* cited by examiner

*Primary Examiner* — Brandon Fetterolf
*Assistant Examiner* — Jean Cornet
(74) *Attorney, Agent, or Firm* — Ladas & Parry LLP

(57) ABSTRACT

The invention provides a novel benzoxazepine compound of the general formula (I):

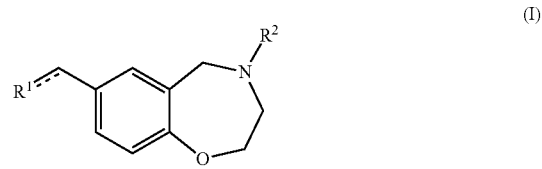

(I)

wherein $R^1$ and $R^2$ are as defined in the specification; or a stereoisomer, a geometric isomer, a pharmaceutically acceptable salt, a pharmaceutically acceptable solvate, or a polymorph thereof; a process for its preparation; and a pharmaceutical composition including an effective amount of the compound. The compounds are useful in the treatment of insulin resistance and clinical conditions associated therewith.

18 Claims, No Drawings

BENZOXAZEPINE COMPOUNDS, THEIR PREPARATION AND USE

This claims the benefit of U.S. Provisional Application No. 60/856,138 filed on 2 Nov. 2006 and incorporates the same by reference.

Field of the Invention

The present invention relates to novel benzoxazepine compounds, to processes for their preparation, to pharmaceutical compositions including the compounds, and to methods employing these compounds, for treating insulin resistance and clinical conditions associated therewith.

BACKGROUND OF THE INVENTION

Diabetes mellitus refers to a durable hyperglycemic condition attributable to the absolute or relative shortage of intrinsic insulin. Diabetes mellitus may be classified as insulin dependent diabetes mellitus (IDDM), that is type 1 diabetes mellitus, for treatment of which insulin administration is absolutely necessary, non insulin-dependent diabetes mellitus (NIDDM), that is type 2 diabetes mellitus, and other diabetes mellitus (secondary diabetes mellitus; diabetes mellitus occurring as one symptom of other diseases). In type 1 diabetes or IDDM, patients produce little or no insulin, the hormone that regulates glucose utilization. In type 2 diabetes or NIDDM, patients often have plasma insulin levels that are the same or even elevated compared to non-diabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

The resistance to insulin responsiveness results in insufficient insulin activation of glucose uptake, oxidation and storage in muscle and inadequate insulin repression of lipolysis in adipose tissue and of glucose production and secretion in the liver.

Metabolic syndrome refers to a cluster of manifestations including insulin resistance with accompanying hyperinsulinemia, type 2 diabetes mellitus, arterial hypertension, central (visceral) obesity, dyslipidemia observed as deranged lipoprotein levels typically characterized by elevated VLDL (very low density lipoprotein) and LDL (low density lipoprotein) and reduced HDL (high density lipoprotein) concentrations and reduced fibrinolysis.

Recent epidemiological research has documented that individuals with insulin resistance run a greatly increased risk of cardiovascular morbidity and mortality, notably suffering from myocardial infarction and stroke. In type 2 diabetes mellitus, atherosclerosis related conditions cause up to 80% of all deaths.

In clinical medicine there is awareness of the need to increase the insulin sensitivity in patients with metabolic syndrome and thus to correct the dyslipidemia which is considered to cause the accelerated progress of atherosclerosis.

The available treatments for type 2 diabetes have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat.

For the treatment of NIDDM, sulfonylurea drugs such as tolbutamide, chlorpropamide and tolazamide, and biguanides such as metformin hydrochloride and buformin have been used as oral blood glucose lowering agents. The morbid state of NIDDM is characterized by insulin deficiency and insulin resistance, and the sulfonylureas stimulating insulin secretion from pancreatic β cells may not be very effective therapeutic medicines for patients with NIDDM condition, where the insulin secretion potential is present, but adequate blood glucose control is not achieved in target organs due to insulin resistance, thus permitting hyperglycemia. The biguanide medicines may permit the onset of lactic acid acidosis, limiting the use of such medicines. Further, these chemicals often cause severe hypoglycemia as a side effect. To address these problems, compounds with a new working mechanism were developed, such as the thiazolidinedione (TZD) derivatives, pioglitazone and rosiglitazone. These TZDs are insulin sensitizers and can ameliorate insulin resistance (or enhance the action of insulin) and lower blood glucose without promoting secretion of insulin from the pancreas. It has been revealed that these TZD-type chemicals induce differentiation of adipocytes, and exhibit their action via an intranuclear receptor PPARγ (peroxisome proliferator-activated receptor gamma: a transcriptional factor important for differentiation of adipocytes) (J. Biol. Chem., 270, 12953-12956, (1995)). By the differentiation of preadipocytes, immature and small adipocytes with less secretion of Tumor Necrosis Factor alpha (TNFα), Free Fatty Acid (FFA) and leptin are increased thus resulting in amelioration of insulin resistance. TZD derivatives also act as agonists for PPARγ, to exhibit the effect of ameliorating insulin resistance.

However, from recent clinical findings using TZD derivatives, conventional synthetic ligands that have PPARγ agonistic activity not only have the activity to improve insulin resistance but also cause disorders of the liver and additionally increase circulating plasma volume in vivo to trigger edema. Since the disorders of liver functions induced by the synthetic PPARγ agonists are serious side effects and the triggering of edema is a very serious side effect causing cardiomegaly, detachment of the main activity, namely insulin-resistance improvement, from such serious side effects is strongly desired.

It is believed that the toxicity of PPARγ agonists described above is derived from the thiazolidinedione moiety, and efforts are being made to design bioisosteres of the TZDs which may retain their useful functions while eliminating the undesired effects. In order to avoid side effects associated with potent PPARγ agonists, partial PPAR agonists are being developed.

Besides PPARγ, PPAR subtypes such as α and δ have been found. PPARγ is located substantially in adipose tissue while PPARα occurs mainly in the liver, heart and kidney, and therefore it was considered that each sub-type has an independent function. In recent years, it has been revealed that PPARγ mainly mediates lipid anabolism by promoting expression of a group of genes for Lipoprotein Lipase (LPL), acyl-CoA carboxylase, Glycerol 3 Phosphate Dehydrogenase (GPDH) etc. to convert glucose into lipid and storing the lipid, while PPARα mediates lipid catabolism by regulating expression of a gene group involved in intake of fatty acids into cells and oxidation thereof to decompose lipid. Moreover, research concerning relationships between particular subtypes of PPAR and various diseases have been widely conducted in recent years (J. Med. Chem., 43(4), 527-550, (2000)).

Compounds having a carboxylic acid moiety in their structure which act as dual agonists of PPARγ and α have also been disclosed.

Many of these dual PPAR α and γ agonists are still in clinical trials and several have been dropped from development due to insufficient efficacy or adverse effects seen in advanced-stage development such as edema, raised levels of hepatic enzymes, renal toxicity, and cancers in animal studies.

Accordingly, there is a need for alternative compounds which are effective in treating insulin resistance without showing the toxic effects of currently available compounds.

U.S. Pat. No. 6,489,322 discloses benzoxazepines having an amidine side chain; the disclosed compounds are inhibitors of Nitric Oxide Synthase. International patent publication no. WO 02/051838 discloses novel benzoxazepine derivatives which are useful as orexin receptor antagonists.

SUMMARY OF THE INVENTION

The present invention provides a benzoxazepine compound of the general formula (I), (I)

wherein:
........(dotted line) represents an optional bond;
$R^1$ is selected from:

where:
$R^3$ and $R^4$ are, independently of each other:
hydrogen; hydroxyl; alkoxy; alkyl; aryl; or amino;
$R^5$, $R^6$ and $R^7$ are, independently of each other:
hydrogen; alkyl; or aryl;
n is 0, 1 or 2; and
the arrows indicate the point of attachment of $R^1$ group;
$R^2$ is selected from:
heteroaryl; heterocyclo; or aryl;

wherein heteroaryl, heterocyclo, or aryl may be unsubstituted or substituted with $R^8$, wherein $R^8$ is, independently of each other:
hydrogen; hydroxyl; alkoxy; $C_1$-$C_4$ alkyl; halogen; amino; or aryl;
or a stereoisomer, geometric isomer, pharmaceutically acceptable salt, pharmaceutically acceptable solvate, or polymorph thereof.

The present invention further provides a process for the preparation of a compound of formula (I), or a stereoisomer, geometric isomer, pharmaceutically acceptable salt, or solvate thereof.

The present invention further provides a compound of the formula (I), or a stereoisomer, geometric isomer, pharmaceutically acceptable salt or solvate thereof, for use as an active therapeutic substance.

The present invention still further provides the use of a compound of the formula (I), or a stereoisomer, geometric isomer, a pharmaceutically acceptable salt or solvate thereof, for the manufacture of a medicament for the treatment of insulin resistance or conditions associated with insulin resistance, especially type 2 diabetes mellitus.

The present invention provides the use of a compound of the formula (I), or a stereoisomer, geometric isomer, a pharmaceutically acceptable salt or solvate thereof, for the treatment of insulin resistance or conditions associated with insulin resistance, especially type 2 diabetes mellitus.

The present invention provides methods of treating insulin resistance or conditions associated with insulin resistance, for example, type 2 diabetes mellitus including administering to a subject in need thereof a compound of the formula (I), or a stereoisomer, geometric isomer, a pharmaceutically acceptable salt or solvate thereof.

The present invention further provides a pharmaceutical composition including a therapeutically effective amount of a compound of the formula (I), or a stereoisomer, geometric isomer, a pharmaceutically acceptable salt or solvate thereof, and a pharmaceutically acceptable carrier or diluent.

DETAILED DESCRIPTION OF THE INVENTION

Definitions

Listed below are definitions of various terms used to describe the compounds of the present invention. These definitions apply to the terms as they are used throughout the specification (unless they are otherwise limited in specific instances) either individually or as part of a larger group.

The term 'alkyl' refers to a straight or branched hydrocarbon chain radical consisting of carbon and hydrogen atoms, containing no unsaturation, having from 1 to 8 carbon atoms, and which is attached to the rest of the molecule by a single bond, e.g., methyl, ethyl, n-propyl, 1-methylethyl (isopropyl), n-butyl, n-pentyl, 1,1-dimethylethyl (t-butyl) and the like. Unless stated otherwise, alkyl groups can be unsubstituted or substituted by one or more identical or different substituents. A substituted alkyl refers to an alkyl residue in which one or more, for example, 1, 2 or 3 hydrogen atoms are replaced with substituents, for example hydroxy, halogen, carboxyl, alkoxycarbonyl, cyano, amino, nitro, oxo (=O), alkyl, alkoxy, aryl, aralkyl, heteroaryl and heterocyclo.

The term "alkoxy" denotes alkyl group as defined above attached via oxygen linkage to the rest of the molecule. Representative examples of those groups are —OCH$_3$, —OC$_2$H$_5$ and the like.

The term "aryl" refers to aromatic radicals having in the range of 6 to 10 carbon atoms such as phenyl, naphthyl, biphenyl and the like.

Unless stated otherwise, aryl residues, for example phenyl or naphthyl, can be unsubstituted or optionally substituted by one or more substituents, for example, up to three identical or different substituents selected from the group consisting of hydroxy, halogen, carboxyl, alkoxycarbonyl, cyano, amino, alkyl, alkoxy, aryl, aralkyl, heteroaryl and heterocyclo.

The term "heterocyclic ring" or "heterocyclo" refers to a stable 3 to 7 membered ring radical which consists of carbon atoms and from one to three heteroatoms selected from the group consisting of nitrogen, oxygen and sulfur. In addition, the nitrogen atom may be optionally quaternized; examples of such heterocyclic ring radicals include, but are not limited to, thiazolidinyl, pyrrolidinyl, tetrahydrofuryl, morpholinyl, pyranyl, dioxolanyl and the like.

Unless stated otherwise, the heterocyclyl groups can be unsubstituted or substituted with one or more (e.g., up to 3), identical or different, substituents. Examples of substituents for the ring carbon and ring nitrogen atoms are hydroxy, halogen, carboxyl, alkoxycarbonyl, cyano, amino, nitro, oxo (=O), alkyl, alkoxy, aryl, aralkyl, heteroaryl and heterocyclo.

The term "heteroaryl," is intended to mean any stable aromatic monocyclic or bicyclic ring where the monocyclic ring has up to 7 ring members and the bicyclic ring has up to 12 ring members. A suitable monocyclic ring has 5 or 6 ring members and the bicyclic ring has 9 or 10 ring members. In the monocyclic or bicyclic rings, from one to three carbon atoms ring members are replaced with heteroatoms selected from: N, O and S. Suitable monocyclic and bicyclic rings contain a N heteroatom and, optionally, one or two further heteroatoms selected from: N, O and S. Examples of heteroaryl elements include, but are not limited to, benzimidazolyl, benzisoxazolyl, benzoxazolyl, furyl, imidazolyl, pyridyl, pyrazinyl, quinolyl, isoquinolyl, oxazolyl, isoxazolyl and the like. The heteroaryl ring radical may be attached to the main structure at any heteroatom or carbon atom that results in the creation of a stable structure.

Unless stated otherwise, the heteroaryl groups can be unsubstituted or substituted with one or more (e.g., up to 3), identical or different, substituents. Examples of substituents for the ring carbon and ring nitrogen atoms are hydroxy, halogen, carboxyl, alkoxycarbonyl, cyano, amino, nitro, alkyl, alkoxy, aryl, aralkyl, heteroaryl and heterocyclo.

The term "aralkyl" refers to an alkyl group substituted with an aryl or heteroaryl group, wherein the terms alkyl, aryl and heteroaryl are as defined above. Exemplary aralkyl groups include —$(CH_2)_p$-phenyl or, —$(CH_2)_p$-pyridyl, wherein p is an integer from 1 to 3.

The term "halogen" refers to radicals of fluorine, chlorine, bromine or iodine.

The term "amino" refers to the group —$NH_2$ which may be optionally substituted with alkoxycarbonyl, amino, alkyl, aryl, aralkyl, heteroaryl and heterocyclo wherein the terms alkyl, aryl, aralkyl, heteroaryl and heterocyclo are as defined herein above.

It will be understood that "substitution" or "substituted with" includes the implicit proviso that such substitution is in accordance with the permitted valence of the substituted atom and the substituent, as well as results in a stable compound, which does not readily undergo transformation such as by rearrangement, cyclization, elimination, etc.

The term "pharmaceutically acceptable salts" means non-toxic salts of the compounds of this invention.

Benzoxazepine Compounds, Methods of Making Them, and Methods Employing Them

The present invention provides compounds of the general formula (I) above.

In an embodiment, the present invention provides compounds of formula (I), wherein:
$R^1$ is selected from:

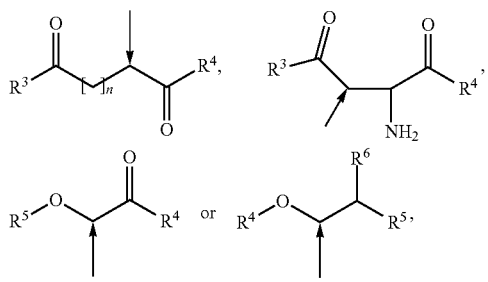

where:
$R^3$ and $R^4$ are, independently of each other:
hydrogen; hydroxyl; alkoxy; $C_1$-$C_4$ alkyl; aryl; or amino;
$R^5$ and $R^6$ are, independently of each other:
hydrogen; $C_1$-$C_4$ alkyl; or aryl;
n is 0, 1 or 2;
the arrows indicate the point of attachment of $R^1$ group; and their stereoisomers, geometric isomers, pharmaceutically acceptable salts and solvates.

In another embodiment, the present invention provides compounds of formula (I),
wherein:
$R^1$ is selected from:

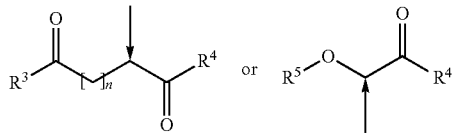

where:
$R^3$ and $R^4$ are, independently of each other:
hydroxyl or alkoxy;
$R^5$ is:
hydrogen; $C_1$-$C_4$ alkyl; or aryl;
n is 0, 1 or 2;
the arrows indicate the point of attachment of $R^1$ group; and their stereoisomers, geometric isomers, pharmaceutically acceptable salts and solvates.

In another embodiment, the present invention provides compounds of formula (I),
wherein:
$R^1$ is:

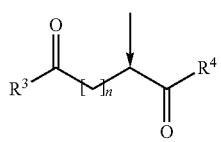

where:
R³ and R⁴ are, independently of each other:
hydroxyl or alkoxy;
n is 0, 1 or 2;
the arrow indicates the point of attachment of R¹ group; and
their stereoisomers, geometric isomers, pharmaceutically acceptable salts and solvates.

In another embodiment, the present invention provides compounds of formula (I),
wherein:
R¹ is selected from:

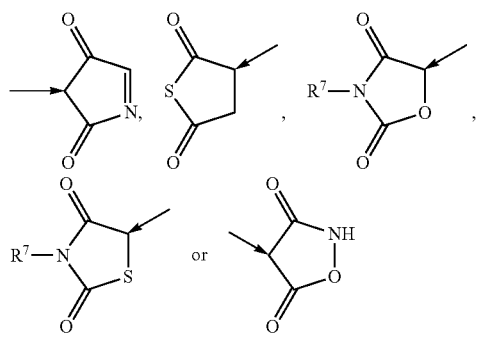

where:
R⁷ is selected from:
hydrogen; $C_1$-$C_4$ alkyl; or aryl;
the arrows indicate the point of attachment of R¹ group; and
their stereoisomers, geometric isomers, pharmaceutically acceptable salts and solvates.

In another embodiment, the present invention provides compounds of formula (I),
wherein:
R¹ is:

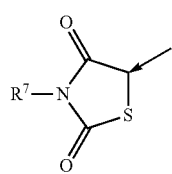

where
R⁷ is:
hydrogen or $C_1$-$C_4$ alkyl;
the arrow indicates the point of attachment of R¹ group; and
their stereoisomers, geometric isomers, pharmaceutically acceptable salts and solvates.

In an embodiment, the present invention provides compounds of formula (I), wherein
R² is heterocyclo selected from:

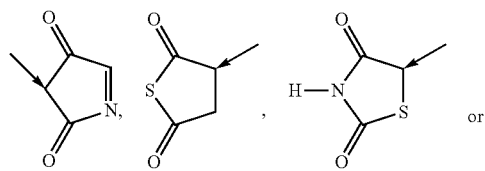

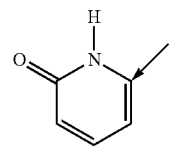

R² is heteroaryl selected from:

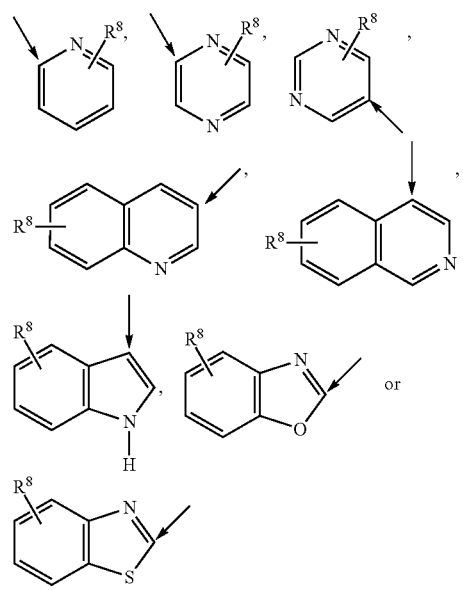

R² is aryl selected from:

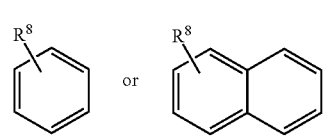

where:
R⁸ is selected from:
hydrogen; hydroxyl; alkoxy; $C_1$-$C_4$ alkyl; halogen; amino; or aryl;
the arrows indicate the point of attachment of R² group to the benzoxazepine core; and
their stereoisomers, geometric isomers, pharmaceutically acceptable salts and solvates.

In another embodiment, the present invention provides compounds of formula (I), wherein
R² is heteroaryl selected from:

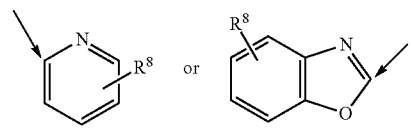

where:
R⁸ is:
hydrogen; hydroxyl; alkoxy; $C_1$-$C_4$ alkyl; halogen; amino; or aryl;

the arrows indicate the point of attachment of R² group to the benzoxazepine core; and their stereoisomers, geometric isomers, pharmaceutically acceptable salts and solvates.

In another embodiment, the present invention provides compounds of formula (I), wherein:

R¹ is selected from:

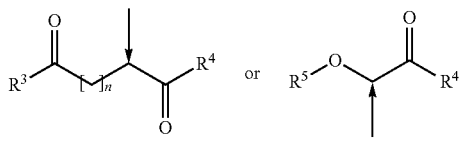

where:
R³ and R⁴ are, independently of each other:
hydroxyl or alkoxy;
R⁵ is:
hydrogen; $C_1$-$C_4$ alkyl; or aryl;
n is 0, 1 or 2;
R² is heteroaryl selected from:

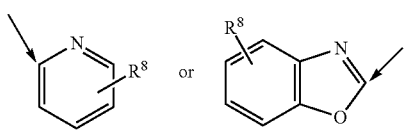

where:
R⁸ is:
hydrogen; hydroxyl; alkoxy; $C_1$-$C_4$ alkyl; halogen; amino; or aryl;
the arrows indicate the point of attachment of R² group to the benzoxazepine core; and
their stereoisomers, geometric isomers, pharmaceutically acceptable salts and solvates.

In another embodiment, the present invention provides compounds of formula (I), wherein:

¹ is selected from:

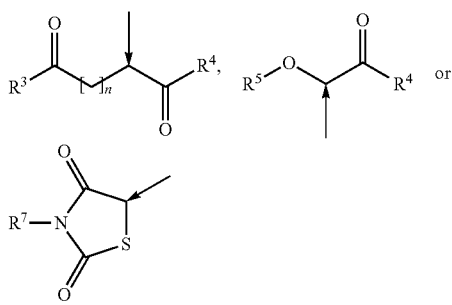

where:
R³ and R⁴ are, independently of each other:
hydroxyl or alkoxy;
R⁵ is:
hydrogen; $C_1$-$C_4$ alkyl; or aryl;
R⁷ is:
hydrogen or $C_1$-$C_4$ alkyl;
n is 0, 1 or 2;

R² is heteroaryl selected from:

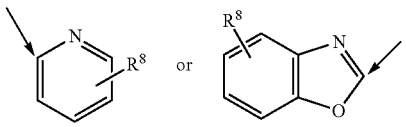

where:
R⁸ is hydrogen; $C_1$-$C_4$ alkyl; or halogen;
the arrows indicate the point of attachment of R² group to the benzoxazepine core; and
their stereoisomers, geometric isomers, pharmaceutically acceptable salts and solvates.

In another embodiment, the present invention provides compounds of formula (I), wherein the optional double bond (--------)is absent.

Compounds of the present invention are selected from but not limited to:
2-(4-pyridin-2-yl-2,3,4,5-tetrahydro-benzo[f][1,4]oxazepin-7-ylmethyl)-malonic acid dimethyl ester,
2-(4-pyridin-2-yl-2,3,4,5-tetrahydro-benzo[f][1,4]oxazepin-7-yl)-methylene)-malonic acid dimethyl ester,
5-(4-pyridin-2-yl-2,3,4,5-tetrahydro-benzo[f][1,4]oxazepin-7-ylmethyl)-thiazolidine-2,4-dione,
5-(4-pyridin-2-yl-2,3,4,5-tetrahydro-benzo[f][1,4]oxazepin-7-yl-methylene)-thiazolidine-2,4-dione,
5-(4-benzooxazol-2-yl-2,3,4,5-tetrahydro-benzo[f][1,4]oxazepin-7-ylmethyl)-thiazolidine-2,4-dione,
5-(4-benzooxazol-2-yl-2,3,4,5-tetrahydro-benzo[f][1,4]oxazepin-7-ylmethylene)-thiazolidine-2,4-dione,
5-(4-pyridine-2-yl-2,3,4,5-tetrahydro-benzo[f][1,4]oxazepin-7-ylmethyl)-thiazolidine-2,4-dione maleate; 5-(4-pyridin-2-yl-2,3,4,5-tetrahydro-benzo[f][1,4]oxazepin-7-ylmethylene)-thiazolidine-2,4-dione maleate; and
their stereoisomers, geometric isomers, pharmaceutically acceptable salts and solvates.

Depending on the process conditions, the end products of the formula (I) are obtained either in neutral or salt form. Both the neutral and salt forms of these end products are within the scope of the invention.

Acid addition salts are generally prepared by reacting compounds of formula (I) having one or more basic groups with a suitable organic or inorganic acid in a suitable solvent.

Representative salts include: hydrobromides, hydrochlorides, sulphates, nitrates, phosphates/diphosphates, perchlorates, borates, acetates, tartrates, maleates, citrates, succinates, methanesulfonates, benzoates, salicylates, benzenesulfonates, ascorbates, fumarates, gluconates, glutamates, malates, mandelates, oxalates, oleates, palmitates, and tosylates.

Compounds of formula (I) having one or more acidic groups are treated with a suitable organic or inorganic base in a suitable solvent to yield pharmaceutically acceptable salts.

Pharmaceutically acceptable salts forming part of this invention include alkali metal salts like Li, Na, and K salts, alkaline earth metal salts like Ca and Mg salts, salts of organic bases such as lysine, arginine, guanidine, diethanolamine, choline and the like, ammonium or substituted ammonium salts, salts of carboxy group wherever appropriate, such as aluminum, alkali metal salts; alkaline earth metal salts, ammonium or substituted ammonium salts.

The compounds of the general formula (I) defined above according to the invention can contain one or more asymmetrically substituted carbon atoms. The presence of one or more of these asymmetric centers in the compounds of the general formula (I) can give rise to stereoisomers and in each case the invention is to be understood to extend to all such stereoisomers, including enantiomers and diastereoisomers and their mixtures, including racemic mixtures.

The present invention includes, wherever possible, E and Z geometrical isomers of the compounds of the general formula (I). The invention is understood to include a single isomer or a mixture of both the isomers.

The present invention includes solvates of the compounds of the formula (I) for example hydrates, and the solvates formed with other solvents of crystallization, such as alcohols, ethers, ethyl acetate, dioxane, DMF, or a lower alkyl ketone, such as acetone, or mixtures thereof.

The present invention also includes polymorphs of the compounds of the general formula (I), as defined below.

According to a further aspect of the invention, there is provided a process for the preparation of a compound of the general formula (I);

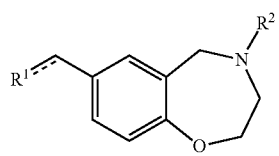

wherein:

_____(dotted line) represents an optional bond;

$R^1$ is selected from:

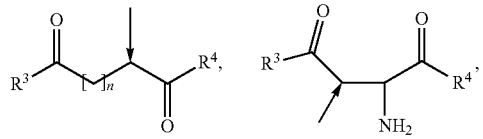

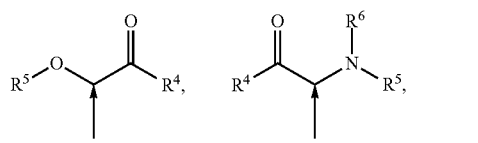

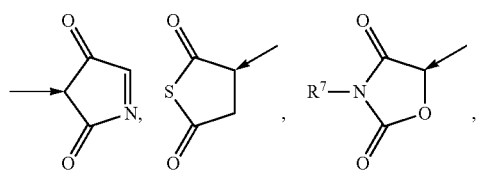

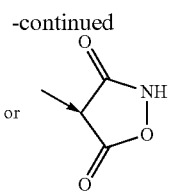

where:

$R^3$ and $R^4$ are, independently of each other:

hydrogen; hydroxyl; alkoxy; $C_1$-$C_4$ alkyl; amino; or aryl;

$R^5$, $R^6$ and $R^7$ are, independently of each other:

hydrogen; $C_1$-$C_4$ alkyl; or aryl;

n is 0, 1 or 2; and the arrows indicate the point of attachment of the $R^1$ group;

$R^2$ is selected from:

heteroaryl; heterocyclo; or aryl;

wherein heteroaryl, heterocyclo, or aryl may be unsubstituted or substituted with $R^8$, wherein $R^8$ is, independently of each other:

hydrogen; hydroxyl; alkoxy; $C_1$-$C_4$ alkyl; halogen; amino; or aryl; and or a stereoisomer, geometric isomer, pharmaceutically acceptable salt, pharmaceutically acceptable solvate, or polymorph thereof;

which process includes:

reacting a compound of formula (II):

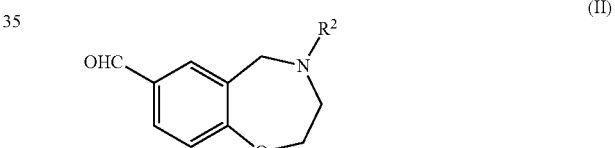

with a compound of the formula $R^1$—H, wherein $R^1$ and $R^2$ are as defined above, to form a compound of the formula (I), wherein the dotted line represents a bond, and, optionally, converting the compound into a pharmaceutically acceptable salt.

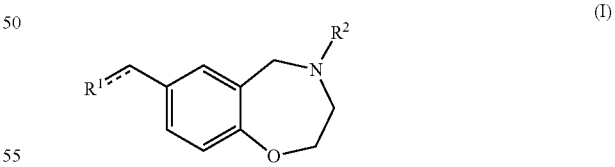

The process described provides a compound of the formula (I), wherein $R^1$ is attached via a double bond, and may further include subjecting the compound to reduction to form a compound of the formula (I), wherein $R^1$ is attached via a single bond, and, optionally, converting the resultant compound into a pharmaceutically acceptable salt.

According to a further feature of the present invention, the compounds of general formula (I) can be prepared by, or in analogy with, standard synthetic methods, and especially according to, or in analogy with, the following scheme:

SCHEME

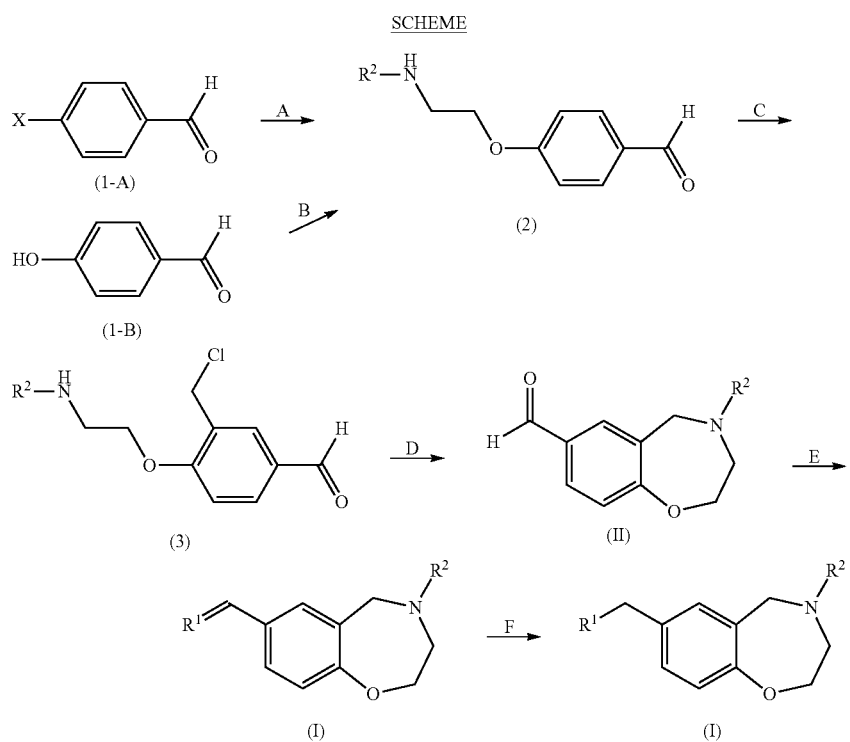

An intermediate used for the preparation of a compound of formula (I) is the compound of formula (2), which may be prepared by the reaction between a compound of formula (1-A), where X is a halide, such as fluoride, and a compound of formula (4);

R²—NH—(CH₂)₂—OH    (4)

in which R² is as defined above in relation to formula (I).

The reaction may be carried out under any suitable conditions, for example in a solvent, such as DMF or DMSO; at an elevated temperature, for example in the range of 100 to 150° C.; suitably in the presence of a base, such as sodium hydride or potassium carbonate (Reaction A of scheme).

Alternatively, the compound of formula (2) may be prepared from a compound of formula (1-B) and a compound of formula (4). The reaction may suitably be carried out in an aprotic solvent, such as THF, and can be done in the presence of a coupling agent, such as that provided by triphenyl phosphine and diethylazodicarboxylate (Reaction B of scheme).

Alternatively, the compound of formula (2) may be prepared from a compound of formula (1-B) and a compound of formula (5);

R²—NH—(CH₂)₂—OY    (5)

in which R² is as defined above in relation to formula (I), and Y represents a leaving group, such as a tosylate or a mesylate group.

The reaction may be carried out in an aprotic solvent, such as DMF, at a low to elevated temperature, for example, in the range of 50° C. to 120° C., and can be done in the presence of a base, such as sodium hydride.

The compound of formula (5) may be prepared from the corresponding compound of formula (4) by reaction with a tosyl halide or a mesyl halide in a solvent, such as pyridine.

The compounds of formula (1-A) or (1-B) are known compounds or are prepared by methods analogous to those used to prepare known compounds; for example, 4-fluorobenzaldehyde and 4-hydroxybenzaldehyde are known commercially available compounds.

The compound of formula (2) may be converted to the compound of formula (3), by chloromethylation using a conventional method; for example, with formaldehyde in the presence of hydrochloric acid and a Lewis acid catalyst, such as zinc chloride, ferric chloride, aluminum chloride, and the like; at a temperature in the range of 10° C. to 50° C., for example, ambient temperature. Duration of the reaction may range from 24 to 72 hours (Reaction C of the scheme above).

The compound of formula (3) may be cyclized to obtain the compound of formula (II) by treating the compound of formula (3) with potassium iodide and/or potassium fluoride optionally in the presence of a base, such as sodium carbonate, potassium carbonate or potassium bicarbonate, in a solvent selected from DMF, dioxane, THF, and the like. The reaction may be carried out at a temperature in the range of 50° C. to 150° C. The duration of the reaction may range from 0.5 to 5 hours (Reaction D of the scheme above).

The compound of formula (II) may be converted to the compound of formula (I), wherein ____ represents a bond, by reacting with R¹—H, wherein R¹ is as defined above in relation to formula (I), in the presence of a Lewis acid catalyst selected from titanium tetrachloride, zinc chloride, ferric chloride, aluminum chloride, and the like; in a solvent selected from chloroform, carbon tetrachloride, tetrahydrofuran, ether, dioxane, or a mixture of two or more of these solvents, under basic conditions. The reaction may be carried out at a temperature in the range of 0° C. to ambient temperature. Duration of the reaction may range from 2 to 24 hours (Reaction E of the scheme above).

Alternatively, the compound of formula (II) may be converted to the compound of formula (I), wherein ---- represents a bond, by reacting with R¹—H, wherein R¹ is as defined above in relation to formula (I), in the presence of piperidinium acetate in toluene refluxed in a Dean Stark apparatus.

The double bond present in the product of the Reaction E may be reduced to give the compound of formula (I) (Reaction F of the scheme above), wherein ---- represents no bond, in the presence of gaseous hydrogen and a catalyst, such as Pd—C, Rh—C, Pt—C, and the like, in the presence of a solvent selected from dioxane, acetic acid, ethyl acetate, and alcohol, such as methanol, ethanol, and the like. The reaction may be carried out at a pressure between atmospheric pressure and 40 psi. The catalyst can be 10% Pd—C. The reaction is carried out at ambient temperature and duration of the reaction may range from 6 to 24 hours.

Alternatively, the reduction may be carried out in the presence of Al-amalgam that is freshly prepared in the presence of a solvent selected from dioxane, 1,2-dimethoxyethane, and the like. The reaction may be carried out at a temperature in the range of −10° C. to 15° C. The duration of the reaction may range from 2 to 6 hours. The reaction may be optionally carried out under an inert atmosphere using nitrogen or argon.

Alternatively, the compound of formula (II) may be converted to a compound of formula (6):

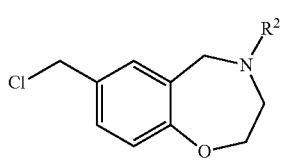

(6)

wherein $R^2$ is as defined above, by reducing the compound of formula (II) to an alcohol, followed by conversion to a haloalkyl compound such as chloroalkyl compound of formula (6) using conventional methods. The compound of formula (6), on reacting with $R^1$—H, wherein $R^1$ is defined in relation to formula (I), under basic conditions, at a temperature range of ambient to 60° C., provides a compound of the formula (I), wherein ---- represents no bond. The present invention further provides an intermediate compound of formula (II):

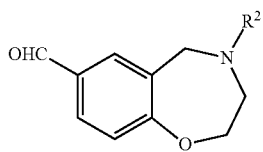

(II)

wherein $R^2$ is as defined above.

The intermediate of formula (II) may be prepared by reacting a compound of formula (3) (above) with a suitable reagent under suitable conditions to effect cyclization of the compound.

The compounds of the present invention may be isolated and purified in a manner known in the art by, for example, distilling off the solvent in vacuum and recrystallizing the residue obtained with a suitable solvent. Moreover, other purification methods, such as column chromatography on a suitable support material, are acceptable techniques. Generally the salts are prepared by contacting the free base or acid of a compound of the formula (I) with a stoichiometric amount, or with an excess, of the desired salt-forming inorganic or organic acid or base in a suitable solvent or dispersant, or by anion exchange or cation exchange with other salts.

Suitable solvents are, for example, ethyl acetate, ether, alcohols, acetone, chlorinated hydrocarbons, THF, dioxane, or a mixture of two or more of these solvents.

The present invention furthermore includes all solvates of the compounds of the formula (I) for example hydrates, and the solvates formed with other solvents of crystallization, such as alcohols, ethers, ethyl acetate, dioxane, DMF, or a lower alkyl ketone, such as acetone, or mixtures thereof.

Various polymorphs of a compound of general formula (I) forming part of this invention may be prepared by crystallization of the compound of formula (I) or its salts under different conditions, for example, using different solvents or their mixtures for recrystallization; crystallizations at different temperatures, various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction, or other such techniques.

The compounds of the present invention were evaluated in in vitro assays including inhibition of gluconeogenesis in isolated rat hepatocytes; adipocyte differentiation in 3T3-L1 cells monitored by potentiation of insulin-stimulated lipogenesis, triglyceride estimation, glycerol-3-phosphate dehydrogenase estimation, or glucose uptake; and PPAR transactivation assays. Certain compounds of the invention were active in assays carried out to evaluate their insulin-sensitizing or insulin-secreting potential. The compounds of the invention are surprisingly not as strongly adipogenic as known TZDs, especially rosiglitazone, and unlike the TZDs are only weak activators of the PPARs, thereby suggesting a better safety profile.

The present invention accordingly provides a compound of formula (I), or a pharmaceutically acceptable salt or solvate thereof, for use as a medicament.

The compounds of the present invention improve insulin sensitivity in insulin resistant mammals. The present invention accordingly provides a compound of the formula (I) for use in the manufacture of a medicament for the treatment of insulin resistance and conditions associated therewith.

The present compounds of formula (I) are useful for the prophylaxis and/or treatment of clinical conditions associated with inherent or induced reduced sensitivity to insulin (insulin resistance) and associated metabolic disorders such as metabolic syndrome. These clinical conditions will include, but will not be limited to hyperinsulinaemia, hyperglycaemia, type 2 diabetes and the dyslipidaemia characteristically appearing with insulin resistance, obesity and arterial hypertension.

Treatment with the present compounds is expected to lower the cardiovascular morbidity and mortality associated with atherosclerosis due to their antidyslipidaemic properties. The cardiovascular disease conditions include: macroangiopathies of various internal organs causing myocardial infarction, congestive heart failure, cerebrovascular disease and peripheral arterial insufficiency of the lower extremities. Because of their insulin sensitizing effect, the compounds of formula (I) are also expected to prevent or delay the development of type 2 diabetes. Therefore, the development of long-term complications associated with chronic hyperglycaemia in diabetes mellitus, such as the micro-angiopathies causing renal disease, retinal damage and peripheral vascular disease of the lower limbs, are expected to be delayed. Furthermore, the compounds may be useful in the treatment of various conditions outside the cardiovascular system whether or not associated with insulin resistance, like polycystic ovarian syndrome, obesity, cancer and states of inflammatory disease, including neurodegenerative disorders, such as mild cognitive impairment, Alzheimer's disease, Parkinson's disease and multiple sclerosis.

The compounds of the present invention are expected to be useful in controlling glucose levels in patients, particularly in patients suffering from type 2 diabetes.

The present invention accordingly provides a method for the treatment or prevention of type 2 diabetes mellitus and conditions associated with diabetes mellitus, including administering to a mammal (e.g., a human) in need thereof, a therapeutically effective amount of a compound of the formula (I), or a pharmaceutically acceptable salt or solvate thereof.

The present invention provides a method for the treatment or prevention of dyslipidemias, the insulin resistance syndrome, metabolic syndrome and/or metabolic disorders (as defined above), including administering to a mammal (e.g., a human) in need thereof, a therapeutically effective amount of a compound of the formula (I), or a pharmaceutically acceptable salt or solvate thereof.

Pharmaceutical Compositions and Methods

As used herein, the terms "treat" and "therapy" and the like refer to alleviate, slow the progression, prophylaxis, attenuation or cure of existing disease (e.g., insulin resistance or type 2 diabetes).

The term "therapeutically effective amount" as used herein is meant to describe an amount of a compound of the present invention effective in producing the desired therapeutic response in a particular patient suffering from insulin resistance or type 2 diabetes.

The pharmaceutical composition may be in the forms normally employed, such as tablets, lozenges, capsules, powders, syrups, solutions, suspensions and the like specially formulated for oral, buccal, parenteral, transdermal, inhalation, intranasal, transmucosal, implant, or rectal administration, however oral administration is preferred. For buccal administration, the formulation may take the form of tablets or lozenges formulated in conventional manner. Tablets and capsules for oral administration may contain conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycolate) or wetting agents, such as sodium lauryl sulfate. The tablets may be coated according to methods well known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides. Additionally, formulations of the present invention may be formulated for parenteral administration by injection or continuous infusion. Formulations for injection may take such forms as suspensions, solutions, or emulsions in oily or aqueous vehicles, and may contain formulatory agents such as suspending, stabilising and/or dispersing agents. Alternatively, the active ingredient may be in powder form for constitution with a suitable vehicle (e.g., sterile, pyrogen-free water) before use.

Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02-5000 mg per day or 1-1500 mg per day. The desired dose may conveniently be presented in a single dose or as divided doses administered at appropriate intervals, for example as two, three, four or more sub-doses per day.

The formulations according to the invention may contain between 0.1-99% of the active ingredient, conveniently from 30-95% for tablets and capsules and 3-50% for liquid preparations.

Furthermore, in addition to at least one compound of the general formula (I), as active ingredient, the pharmaceutical compositions may also contain one or more other therapeutically active ingredients.

According to an embodiment of the present invention, there is provided a method for the treatment of insulin resistance or conditions associated with insulin resistance, including administering to a mammal in need thereof a therapeutically effective amount of a compound of formula (I).

According to an embodiment of the present invention there is provided a method for the treatment of the insulin resistance or conditions associated with insulin resistance, including type 2 diabetes mellitus, lipid and carbohydrate metabolism disorders, dyslipidemia, hyperinsulinemia, glucose intolerance, atherosclerosis or obesity, including administering to a mammal in need thereof a therapeutically effective amount of a compound of formula (I).

According to an embodiment of the present invention, there is provided a method for the treatment of type 2 diabetes mellitus, including administering to a mammal in need thereof a therapeutically effective amount of a compound of formula (I).

According to an embodiment, the compounds of present invention are useful for the treatment of insulin resistance or conditions associated with insulin resistance.

According to an embodiment, the compounds of the present invention are useful for the treatment of the insulin resistance or conditions associated with insulin resistance, including type 2 diabetes mellitus, lipid and carbohydrate metabolism disorders, dyslipidemia, hyperinsulinemia, glucose intolerance, atherosclerosis or obesity. According to an embodiment, the compounds of the present invention are useful for the treatment of type 2 diabetes.

It is understood that modifications that do not substantially affect the activity of the various embodiments of this invention are included within the invention disclosed herein.

Accordingly, the following examples are intended to illustrate but not to limit the present invention. Without further elaboration, it is believed that one skilled in the art can, based on the description herein, utilize the present invention to its fullest extent.

EXAMPLES

The following abbreviations are used herein:

| | |
|---|---|
| THF | Tetrahydrofuran |
| EtOAc | Ethyl acetate |
| MeOH | Methanol |
| $CCl_4$ | Carbon tetrachloride |
| $CH_2Cl_2$ | Dichloromethane |
| DMF | Dimethyl formamide |
| HCl | Hydrochloric acid |
| NaOH | Sodium hydroxide |
| $CO_2$ | Carbon dioxide |

Example 1

2-(4-Pyridin-2-yl-2,3,4,5-tetrahydro-benzo[f][1,4]oxazepin-7-ylmethylene)-malonic acid dimethyl ester Step I Preparation of 4-[2-(pyridin-2-yl-amino)-ethoxy]-benzaldehyde Preparation of 4-[2-(pyridin-2-ylamino)-ethoxy]-benzaldehyde is known in the literature, and may be prepared by published procedures or by methods well known to one skilled in the art, for example by reacting 4-fluorobenzaldehyde and 2-(pyridin-2-yl-amino)-ethanol as per the procedure in J. Med. Chemistry 37, 3977-3985, 1994.

Step II

Preparation of 3-chloromethyl-4-[2-(pyridin-2-yl-amino)-ethoxy]-benzaldehyde

4-[2-(Pyridin-2-yl-amino)-ethoxy]-benzaldehyde [compound of Step I] (11.9 g, 49.17 mmol) was dissolved in 170 ml concentrated HCl, and to this solution were added zinc chloride (2.54 g, 18.6 mmol) and formaldehyde (12.95 mL of 35% aqueous solution, 151 mmol). HCl gas was passed through the reaction mixture for 5 hours. The reaction mixture was stirred for 64 hours. The reaction mixture was diluted with 3 L water. The resulting solution was carefully neutralised with 50% aqueous NaOH (pH 7-8), maintaining the temperature of reaction mixture below room temperature by external cooling. The resulting solution was extracted with ethyl acetate (2×1.5 L). The extract was washed with 1.5 L brine, dried over anhydrous sodium sulfate and concentrated at 40° C. under vacuum to give 3-chloromethyl-4[2-(pyridin-2-yl-amino)-ethoxy]-benzaldehyde.

Yield: 7.45 g (52.2%).

$^1$H NMR ($CDCl_3$): δ 9.9 (s, 1H), 8.11 (d, 1H), 7.9 (br.s, 1H), 7.86 (dd, 1H), 7.42 (m, 1H), 7.04 (d, 1H), 6.61 (m, 1H), 6.48 (d, 1H), 5.3 (br.s, 1H, exchangeable), 4.72 (s, 2H), 4.35 (t, 2H), 3.9 (m, 2H)

Step III

Preparation of 4-pyridin-2-yl-2,3,4,5-tetrahydro-benzo[f][1,4]oxazepine-7-carbaldehyde To a solution of 3-chloromethyl-4-[2-(pyridin-2-yl-amino)-ethoxy]-benzaldehyde [compound of step II] (7.45 g, 25.7 mmol) in 340 mL DMF, was added potassium iodide (8.53 g, 51.4 mmol) and the reaction mixture was heated to 130° C. for 1 hour. The reaction mixture was cooled, diluted with 1 L water and extracted with 2×500 mL of ethyl acetate. The ethyl acetate extract was washed with 250 mL brine, dried over anhydrous sodium sulfate and concentrated under vacuum at 40° C. to give 5.9 g crude material. This crude material was purified by silica chromatography using 15% ethyl acetate in petroleum ether to give 4-pyridin-2-yl-2,3,4,5-tetrahydro-benzo [f][1,4]oxazepine-7-carbaldehyde.

Yield: 0.872 g (13.4%).

$^1$H NMR ($CDCl_3$): δ 9.93 (s, 1H), 8.14 (m, 1H), 7.9 (br.s, 1H), 7.7 (dd, 1H), 7.45 (m, 1H), 7.12 (d, 1H), 6.66 (d, 1H), 6.58 (m, 1H), 4.84 (s, 2H), 4.3 (m, 2H), 4.2 (m, 2H)

Step IV

Preparation of 2-(4-pyridin-2-yl-2,3,4,5-tetrahydro-benzo[f][1,4]oxazepin-7-yl)-methylene)-malonic acid dimethyl ester Titanium tetrachloride (190 mg, 1 mmol) in 2.5 mL $CCl_4$ was added to 20 mL dry THF at 0° C. and to this solution, were added 4-pyridin-2-yl-2,3,4,5-tetrahydro-benzo [f][1,4]oxazepine-7-carbaldehyde [compound of Step III] (127 mg; 0.5 mmol) in 1 mL THF and dimethyl malonate (66 mg, 0.5 mmol) at 0° C. To the reaction mixture was added a solution of pyridine (158 mg, 2 mmol) in 3.5 mL THF over a period of half hour at 0° C. and stirred at room temperature for 16 hours. Further, the reaction mixture was poured in 250 mL ice-cold water and extracted with diethyl ether (2×100 mL). The extract was then washed with saturated sodium bicarbonate solution (2×100 mL), brine (2×100 mL) and dried over anhydrous sodium sulfate. The solution was then concentrated at 40° C. under vacuum, to give 100 mg crude material, which was purified by silica chromatography using 15% ethyl acetate in petroleum ether to give 2-(4-pyridin-2-yl-2,3,4,5-tetrahydro-benzo[f][1,4]oxazepin-7-yl)-methylene)-malonic acid dimethyl ester.

Yield: 70 mg (38%).

$^1$H NMR (DMSO $d_6$): δ 8.1 (dd, 1H), 7.7 (s, 1H), 7.6 (br.s, 1H), 7.5 (t, 1H), 7.3 (dd, 1H), 7.0 (d, 1H), 6.8 (d, 1H), 6.55 (m, 1H), 4.81 (s, 2H), 4.24 (br.t, 2H), 4.08 (br.t, 2H), 3.87 (s, 3H), 3.8 (s, 3H).

Example 2

2-(4-Pyridin-2-yl-2,3,4,5-tetrahydro-benzo[f][1,4]oxazepin-7-yl)-methyl)-malonic acid dimethyl ester 2(4-Pyridin-2-yl-2,3,4,5-tetrahydro-benzo[f][1,4]oxazepin-7-yl)-methylene)-malonic acid dimethyl ester [compound of Example 1] (36.8 mg, 0.1 mmol) was dissolved in 15 mL MeOH, to which was added 10% Pd—C (5 mg). The mixture was subjected to hydrogenation at 10 psi for 20 hours. The reaction mixture was filtered through celite and concentrated at 40° C., under vacuum to give 2-(4-pyridin-2-yl-2,3,4,5-tetrahydro-benzo[f][1,4]oxazepin-7-yl)-methyl)-malonic acid dimethyl ester.

Yield: 10 mg (27%).

$^1$H NMR (DMSO $d_6$): δ 8.05 (br.d, 1H), 7.47 (br.t, 1H), 7.3 (d, 1H), 7.0 (br.d, 1H), 6.85 (d, 2H), 6.56 (br.t, 1H), 4.69 (s, 2H), 4.06 (br.s, 4H), 3.84 (t, 1H), 3.6 (s, 6H), 3.04 (d, 2H)

Example 3

5-(4-Pyridin-2-yl-2,3,4,5-tetrahydro-benzo[f][1,4] oxazepin-7-ylmethylene)-thiazolidine-2,4-dione 4-Pyridin-2-yl-2,3,4,5-tetrahydro-benzo[f][1,4]oxazepine-7-carbaldehyde [compound of Example 1-Step III] (0.868 g, 3.4 mmol) was dissolved in 100 mL dry toluene and to this solution, was added 2,4-thiazolidinedione (0.402 g, 3.4 mmol) and piperidinium acetate (46 mg, 0.32 mmol). The reaction mixture was refluxed in a Dean Stark apparatus for 4 hours. The reaction mixture was cooled and filtered. The residue was washed with petroleum ether (500 mL) and dried in air to give crude material A (0.6 g). The filtrate and petroleum ether wash were combined, cooled overnight and filtered. The filtrate was washed with petroleum ether (500 mL). The residue was dried in air to give crude material B (0.24 g). Both crude materials, A and B were combined and purified by silica chromatography using 1% $CH_2Cl_2$ in MeOH to give 5-(4-pridin-2-yl-2,3,4,5-tetrahydro-benzo[f][1,4]oxazepin-7-ylmethylene)-thiazolidine-2,4-dione.

Yield: 0.54 g (45%).

mp: 260-261° C.; IR (KBr): 3400, 1710, 1610, 1580, 1515, 1260 $cm^{-1}$; $^1$H NMR (DMSO $d_6$): δ 12.5 (s, 1H, exchangeable), 8.07 (m, 1H), 7.74 (s, 1H), 7.72 (m, 1H), 7.5 (t, 1H), 7.4(d, 1H), 7.08 (d, 1H), 6.9 (d, 1H), 6.58 (t, 1H), 4.86 (s, 2H), 4.22 (m, 2H), 4.1(m, 2H)

Example 4

5-(4-Pyridin-2-yl-2,3,4,5-tetrahydro-benzo[f][1,4] oxazepin-7-yl-methyl)-thiazolidine-2,4-dione 5-(4-Pyridin-2-yl-2,3,4,5-tetrahydro-benzo[f][1,4]oxazepin-7-ylmethylene)-thiazolidine -2,4-dione [compound of Example 3] (0.54 g, 1.5 mmol) was taken in 1,2-dimethoxyethane (45 mL) and heated to dissolve. The reaction mixture was then cooled to −5 to 0° C. and to this solution kept under nitrogen, were added pieces of aluminum foil (10×10×0.02 mm, 0.306 g, 11.3 mmol) which had been freshly dipped for 10 seconds sequentially in each of diethyl ether, ethanol, 2% aqueous mercuric chloride solution, ethanol and again diethyl ether. To the reaction mixture, water was added (0.45 mL), and stirred for 3.5 hours at −5 to 0° C. under $N_2$ atmosphere. To this solution, celite (2.4 g) was added, stirred at room temperature for 5 min, filtered through a celite bed and washed with DMF (3×60 mL). The filtrate was concentrated to give crude material (0.820 g) which was purified by silica chromatography using 1% $CH_2Cl_2$ in MeOH, to give 5-(4-pyridin-2-yl-2,3,4,5-tetrahydro-benzo[f][1,4]oxazepin-7-yl-methyl)-thiazolidine-2,4-dione.

Yield: 0.282 g (53%).

mp: 180-181° C.; IR (KBr): 3440, 1750, 1710, 1605, 1490 $cm^{-1}$; $^1$H NMR (CDCl$_3$): δ 8.13 (d, 1H), 7.44 (t, 1H), 7.23 (d, 1H), 7.03 (br.d, 1H), 6.96 (d, 1H), 6.64 (d, 1H), 6.6 (t, 1H), 4.71 (s, 2H), 4.5 (dd, 1H), 4.05-4.25 (m, 2H), 3.47 (dd, 2H), 3.13 (dd, 2H)

Example 5

5-(4-Pyridine-2-yl-2,3,4,5-tetrahydro-benzo[f][1,4] oxazepin-7-ylmethyl)-thiazolidine-2,4-dione maleate 5-(4-Pyridine-2-yl-2,3,4,5-tetrahydro-benzo[f][1,4]oxazepin-7-ylmethyl)-thiazolidine-2,4-dione [compound of Example 4] (260.2 mg, 0.730 mmol) was dissolved in methanol (20 mL). To this solution, maleic acid (85 mg, 0.730 mmol) was added under stirring at room temperature to give a turbid solution. On warming to 40° C., both the components dissolved completely. It was then diluted with methanol (10 mL) and stirred overnight. The reaction mixture was filtered and concentrated to give a yellow oil. The oil was dried under high vacuum at 40° C. for 2 hours to give a yellow crystalline solid.

Yield: 300 mg (83.7%).

mp: 74-76° C.; $^1$H NMR (CDCl$_3$+DMSO $d_6$): δ 11.5 (br.s, 1H), 7.85 (d, 1H), 7.25 (t, 1H), 7.00 (s, 1H), 6.75 (d, 1H), 6.65 (d, 1H), 6.45 (d, 1H), 6.35 (t, 1H), 6.05 (s, 2H), 4.42 (s, 2H), 4.25 (dd, 1H), 4.05-3.85(m, 4H), 3.18 (dd, 1H), 2.80 (dd, 1H).

Example 6

5-(4-Benzooxazol-2-yl-2,3,4,5-tetrahydro-benzo[f] [1,4]oxazepin-7-ylmethylene)-thiazolidine-2,4-dione Step I Preparation of 2-methylsulfanyl-benzooxazole Methyl iodide (20 mL, 320 mmol) was added to a solution of benzooxazole-2-thiol (25.0 g, 165 mmol) taken in dry THF (250 mL) and the reaction mixture was stirred at room temperature for 80 hours, after which it was concentrated to give 2-methylsulfanyl-benzooxazole.

Yield: 25.0 g (91.50%).

Mass (EI): 165 (M$^+$); $^1$H NMR (CDCl$_3$): δ 7.60 (d, 1H), 7.42 (d, 1H), 7.26 (m, 2H), 2.80 (s, 3H).

Step II

Preparation of 2-(benzooxazol-2-ylamino)-ethanol

To 2-methylsulfanyl-benzooxazole [compound of Step I] (25 g, 150 mmol), ethanolamine (253 g, 250 mL) was added and the reaction mixture was heated at 100° C. for 1.5 hours. The reaction mixture was poured on crushed ice-water mixture and extracted with ethyl acetate (3×1 L). The ethyl acetate layer was washed with water and brine, dried over anhydrous sodium sulfate and concentrated to give 2-(benzooxazol-2-ylamino)-ethanol.

Yield: 10.0 g (37.09%).

Mass (EI): 178 (M$^+$); $^1$H NMR (DMSO $d_6$): δ 7.95 (t, 1H), 7.35 (d, 1H), 7.23 (d, 1H), 7.15 (t, 1H), 6.95 (t, 1H), 4.83 (t, 1H), 3.58 (m, 2H), 3.35 (m, 2H).

Step III

Preparation of sulfurous acid 2-(benzooxazol-2-ylamino)-ethyl ester methyl ester 2-(Benzooxazol-2-ylamino)-ethanol [compound of Step II] (9.76 g, 55 mmol) was taken in dry pyridine (40 mL) and to this solution, methanesulfonyl chloride (4.6 mL, 60 mmol) was added under stirring at room temperature. The reaction mixture was stirred for 15 hours, then diluted with ice water and extracted with dichloromethane (3×200 mL). The dichloromethane layer was washed with water and brine, dried over anhydrous sodium sulfate and was concentrated to give a crude material (18 g). The crude material obtained was purified using a silica gel column and 80% ethyl acetate in petroleum ether to yield sulfurous acid 2-(benzooxazol-2-ylamino)-ethyl ester methyl ester.

Yield: 13.0 g (92.72%)

Mass (EI): 256 (M$^+$); $^1$H NMR (CDCl$_3$): δ 7.40 (d, 1H), 7.25 (d, 1H), 7.15 (t, 1H), 7.09 (t, 1H), 4.45 (t, 2H), 3.85 (t, 2H), 3.05 (s, 3H).

Step IV

Preparation of
4[2-(benzooxazol-2-ylamino)-ethoxy]-benzaldehyde

To a mixture of 4-hydroxybenzaldehyde (6.1 g, 50 mmol) in dry DMF (40 mL), was added sodium hydride (2.2 g, 55 mmol, 60% suspension) under stirring, in a nitrogen atmosphere at room temperature. The thick solution was diluted with dry DMF (20 mL). Sulfurous acid 2-(benzooxazol-2-ylamino)-ethyl ester methyl ester [compound of Step III] (14 g, 55 mmol) dissolved in dry DMF was added dropwise to the reaction mixture over a period of 20 min and the resulting mixture was heated to 80° C. for 1 hour. The reaction mixture was poured on crushed ice and then extracted with ethyl acetate (3×200 mL). The ethyl acetate layer was washed with water and brine, dried over anhydrous sodium sulfate, concentrated and purified using silica gel column and 50% ethyl acetate in petroleum ether to give 4-[2-(benzooxazol-2-ylamino)-ethoxy]-benzaldehyde.

Yield: 3.6 g (23.35%).

Mass (EI): 282 (M$^+$); $^1$H NMR (CDCl$_3$): δ 9.90 (s, 1H), 7.85 (d, 2H), 7.40 (d, 1H), 7.30 (d, 1H), 7.20 (t, 1H), 7.10 (d, 1H), 7.00 (d, 2H), 4.30 (t, 2H), 3.95 (t, 2H).

Step V

Preparation of 4-[2-(benzooxazol-2-ylamino)-ethoxy]-3-chloromethyl-benzaldehyde

To 4-[2-(benzooxazol-2-ylamino)-ethoxy]-benzaldehyde [compound of Step IV] (3.52 g, 12.5 mmol) taken in concentrated HCl (150 mL), were added, zinc chloride (0.650 g, 4.76 mmol) and formaldehyde solution (3.2 mL of 35% aqueous solution, 37.3 mmol) and the resulting mixture was stirred at room temperature. HCl gas was bubbled into the reaction mixture at a constant rate until the mixture was saturated (for about 4 hours.), Stirring was continued for 55 hours at room temperature. The resulting mixture was poured on crushed ice, and neutralized to pH 7.5-8.0 with 50% NaOH solution, extracted with ethyl acetate (3×200 mL), washed with water, dried over anhydrous sodium sulfate, concentrated, and crystallized from ethyl acetate/petroleum ether to give 4-[2-(benzooxazol-2-ylamino)-ethoxy]-3-chloromethyl-benzaldehyde.

Yield: 2.25 g (54.61%).

Mass (EI): 330 (M$^+$); $^1$H NMR (CDCl$_3$): δ 9.92 (s, 1H), 7.9 (br.s, 1H), 7.85 (d, 1H), 7.40 (d, 1H), 7.25 (d, 1H), 7.15 (t, 1H), 7.05 (m, 2H), 4.70 (s, 2H), 4.40 (t, 2H), 4.00 (br.t, 2H).

Step VI

Preparation of 4-benzooxazol-2-yl-2,3,4,5-tetrahydro-benzo[f][1,4]oxazepine-7-carbaldehyde To 4[2-(benzooxazol-2-ylamino)-ethoxy]-3-chloromethyl-benzaldehyde [compound of Step V] (3.3 g, 10 mmol) taken in dry DMF (100 mL), were added potassium carbonate (4.14 g, 30 mmol) and potassium iodide (3.32 g, 20 mmol). The reaction mixture was stirred at room temperature for 55 hours. The reaction mixture was diluted with water and extracted with ethyl acetate (3×200 mL). The ethyl acetate layer was washed with water and brine, dried over anhydrous sodium sulfate and concentrated. The brown oil (4.0 g) obtained was purified using silica gel column and 30% ethyl acetate in petroleum ether to yield the desired product 4-benzooxazol-2-yl-2,3,4,5-tetrahydro-benzo[f][1,4]oxazepine-7-carbaldehyde.

Yield: 0.085 g (2.89%).

Mass (EI): 294 (M$^+$); $^1$H NMR (CDCl$_3$): δ 9.95 (s, 1H), 8.00 (br.s, 1H), 7.78 (d, 1H), 7.32 (m, 2H), 7.18 (m, 2H), 7.05 (m, 1H), 4.90 (br.s, 2H), 4.35 (m, 2H), 4.18 (m, 2H).

Step VII

Preparation of 5-(4-benzooxazol-2-yl-2,3,4,5-tetrahydro-benzo[f][1,4]oxazepin-7-yl-methylene)-thiazolidine-2,4-dione To 4-benzooxazol-2-yl-2,3,4,5-tetrahydro-benzo[f][1,4]oxazepine-7-carbaldehyde [compound of Step VI] (0.176 g, 0.6 mmol) taken in toluene (25 mL) were added 2,4-thiazolidine dione (0.105 g, 0.9 mmol) and catalytic amount of piperidinium acetate (0.025 g). The resulting mixture was refluxed under Dean Stark conditions for 1.5 hours and then cooled in an ice-bath. The precipitate was filtered and washed with toluene and petroleum ether to give 5-(4-benzooxazol-2-yl-2,3,4,5-tetrahydro-benzo[f][1,4]oxazepin-7-ylmethylene)-thiazolidine-2,4-dione.

Yield: 0.150 g (63.83%).

Mass (EI): 393 (M$^+$); $^1$H NMR (DMSO d$_6$): δ 7.65 (s, 1H), 7.6 (s, 1H), 7.40 (t, 2H), 7.30 (d, 1H), 7.1 (m, 2H), 7.00 (t, 1H), 4.85 (s, 2H), 4.32 (t, 2H), 4.18 (m, 2H).

Example 7

5-(4-Benzooxazol-2-yl-2,3,4,5-tetrahydro-benzo[f][1,4]oxazepin-7-yl-methyl)-thiazolidine-2,4-dione a) Preparation of Al-Amalgam Strip.

Aluminum foil (0.056 g, 2.1 mmol) was cut into fine strips, washed sequentially for 10 seconds each with diethyl ether, then with ethanol and then in 2% aqueous mercuric chloride solution followed by ethanol and diethyl ether. The strip after this treatment was cut into fine pieces and used as freshly prepared Al-amalgam strips.

b) 5-(4-Benzooxazol-2-yl-2,3,4,5-tetrahydro-benzo[f][1,4]oxazepin-7-ylmethylene)-thiazolidine-2,4-dione [compound of Example 6] (0.118 g, 0.3 mmol) was taken in 1,2-dimethoxyethane (40 mL) under nitrogen. The mixture was cooled to 7-10° C. by using dry ice-acetone bath, freshly prepared Al-amalgam strips and water (0.54 mL, 30 mmol) were added and the reaction mixture was stirred for 4 hours. The reaction mixture was then filtered through a celite bed and washed with 1,2-dimethoxyethane. The organic layer was concentrated under high vacuum and purified using silica gel column in 50% ethyl acetate in petroleum ether. The product obtained after concentration was washed with 2% ethyl acetate in petroleum ether, to give 5-(4-benzooxazol-2-yl-2,3,4,5-tetrahydro-benzo[f][1,4]oxazepin-7-ylmethyl)-thiazolidine-2,4-dione.

Yield: 0.015 g (12.71%).

Mass (EI): 395 (M$^+$); $^1$H NMR (CDCl$_3$): δ 8.0 (br.s, 1H), 7.3 (m, 3H), 7.15 (m, 1H), 7.05 (m, 3H), 4.75 (d, 2H), 4.50 (dd, 1H), 4.15 (m, 4H), 3.48 (dd, 1H), 3.16 (dd, 1H).

Example 8

5-(4-Pyridin-2-yl-2,3,4,5-tetrahydro-benzo[f][1,4]oxazepin-7-ylmethylene)-thiazolidine-2,4-dione maleate To a mixture of 5-(4-Pyridin-2-yl-2,3,4,5-tetrahydro-benzo[f][1,4]oxazepin-7-ylmethylene)-thiazolidine-2,4-dione [compound of Example 3] (35.3 mg, 0.1 mmol) and maleic acid (11.6 mg, 0.1 mmol) in a 100 mL two necked round bottomed flask was added 30 mL methanol:dichloromethane (2:1). The mixture was heated until a clear solution was obtained. The solution was stirred overnight (16 hours) and concentrated to give a solid which was recrystallized from methanol:dichloromethane:petroleum ether to give crystals of 5-(4-Pyridin-2-yl-2,3,4,5-tetrahydro-benzo[f][1,4]oxazepin-7-ylmethylene)-thiazolidine-2,4-dione maleate. mp: 224-226° C.

Pharmacology

Example 9

Effect on Gluconeogenesis in Isolated Rat Hepatocytes
Assay protocol for determination of inhibition of gluconeogenesis by compounds in isolated rat hepatocytes:
a) Isolation of Rat Hepatocytes
Hepatocytes were isolated by collagenase digestion of perfused livers from male Wistar rats fasted overnight according to the method described in J. Cell. Science., 56, 233-244, 1982, the disclosure of which is incorporated by reference for the teaching of the method.
b) Study of Gluconeogenesis in Hepatocytes
The assay was done in three groups: basal, control and test. The test compounds were added to the vials at different concentrations. The isolated hepatocytes were added to the vials and they were incubated at 37° C. for 15 min. After 15 min, 5 mM fructose (precursor for gluconeogenesis) was added to the control and test group. Vials were again incubated at 37° C. for one hour with constant shaking (80 cycles/min.). Incubation was terminated by centrifuging the reaction mixture at 3000 rpm for 5 min. The supernatant was used for determination of both glucose and lactate dehydrogenase (LDH) (Table 1).
An active compound would decrease the amount of glucose formed, which is read at 520 nm by glucose oxidase-peroxidase method.
The LDH activity is measured, by the method described in Meth. Enz. Ana. 3, 118-125, 1984, the disclosure of which is incorporated by reference for the teaching of the method, as the amount of pyruvate consumed by continuously monitoring the decrease in absorbance due to oxidation of NADH (Nicotinamide Adenine Dinucleotide-reduced form) at 339 nm.

TABLE 1

Inhibition of gluconeogenesis in isolated rat hepatocytes

| Expt No | Test Compound | Concentration ($\mu$M) | Gluconeogenesis (glucose production) % inhibition | LDH % leakage |
|---|---|---|---|---|
| 1 | Rosiglitazone | 5 | 11 | 9 |
|  |  | 10 | 28 | 9 |
|  |  | 25 | 43 | 10 |
|  |  | 50 | 57 | 11 |
|  |  | 100 | 68 | 15 |
| 2 | Compound of Example 3 | 10 | 10 | 5 |
|  |  | 25 | 36 | 5 |
|  |  | 50 | 42 | 6 |
|  |  | 75 | 51 | 7 |
|  |  | 100 | 74 | 7 |
| 3 | Compound of Example 4 | 10 | 27 | No leakage |
|  |  | 50 | 35 |  |
|  |  | 100 | 57 |  |

TABLE 1-continued

Inhibition of gluconeogenesis in isolated rat hepatocytes

| Expt No | Test Compound | Concentration ($\mu$M) | Gluconeogenesis (glucose production) % inhibition | LDH % leakage |
|---|---|---|---|---|
| 4 | Compound of Example 7 | 3 | 12 | No leakage |
|  |  | 30 | 19 |  |
|  |  | 100 | 50 |  |
| 5 | Compound of Example 8 | 10 | 9 | No leakage |
|  |  | 50 | 13 |  |
|  |  | 100 | 45 |  |

Example 10

Insulin Sensitizing Assay Employing 3T3-L1 Adipocytes
3T3-L1 pre-adipocytes were grown to confluence in 25 ml culture flasks in DMEM (Dulbecco's Modified Eagle's Medium, with 25 mM glucose) containing 10% fetal calf serum (FCS) and antibiotics in a humidified atmosphere of 5% $CO_2$ and 95% air at 37° C. The medium was changed every 2-3 days. The cells were trypsinised at confluency using 0.25% trypsin and transferred to another flask.
For the assay, cells were grown in 24 well plates. Induction of differentiation was done when the cells had grown to confluency with DMEM containing 5% FCS and supplemented with 0.5 mM IBMX (3-Isobutyl-1-methylxanthine), 0.5 $\mu$M DEX (dexamethasone) and 1 $\mu$g/ml insulin. After two days of incubation, the medium was replaced with fresh medium containing 100 nM insulin with standard rosiglitazone or test compounds and control wells containing medium with either insulin alone or standard TZD (thiazolidinedione) or test compound alone. The medium was changed three times, each at an interval of 2 days. On the day of termination of medium changes, lipogenesis assay was performed.
Lipogenesis Assay in 3T3-L1 Adipocytes
3T3-L1 cells were grown to confluency in 24 well plates. They were induced to differentiate for two days and then treated with standard rosiglitazone and test compounds by replenishing media at intervals of two days. On the day of termination of the assay the cells were incubated in 3 ml/well KRHB (Krebs-Ringer Hepes buffer) for 2 hr at 37° C. in a $CO_2$ incubator. This was replaced with fresh KRHB with 0.1 mM glucose containing 100 nM insulin, test compound or insulin plus test compound. Lipogenesis was initiated by the addition of 20 $\mu$l of 50 $\mu$Ci/ml [$^3$H]-D-Glucose to each well and incubation for 90 min at 37° C. in a $CO_2$ incubator. The reaction was terminated by aspirating the medium from each well and washing the cells rapidly 3 times with ice-cold PBS (phosphate buffered saline). 500 $\mu$l of 0.2 N NaOH was added to lyse the cells. 450 $\mu$l was aliquoted into scintillation vials and scintillation cocktail added. The vials were read in Liquid Scintillation Counter. Results are expressed as fold activation of the standard or test compound over the control (Table 2).

Table 2

Potentiation of insulin-stimulated lipogenesis in 3T3-L1 pre-adipocytes by test compounds

| Expt No | Treatment | Fold stimulation |
|---|---|---|
| 1 | Insulin | 1 |
|  | Insulin + rosiglitazone (10 $\mu$M) | 2.4 |
|  | Insulin + Compound of Example 3 (1 $\mu$M) | 1.2 |

Table 2-continued

Potentiation of insulin-stimulated lipogenesis in 3T3-L1 pre-adipocytes by test compounds

| Expt No | Treatment | Fold stimulation |
|---|---|---|
|   | Insulin + Compound of Example 3 (10 μM) | 1.4 |
|   | Insulin + Compound of Example 3 (25 μM) | 1.7 |
| 2 | Insulin | 1 |
|   | Insulin + rosiglitazone (10 μM) | 3 |
|   | Insulin + Compound of Example 6 (10 μM) | 1.4 |
| 3 | Insulin | 1 |
|   | Insulin + rosiglitazone (10 μM) | 3.6 |
|   | Insulin + Compound of Example 4 (10 μM) | 2 |
|   | Insulin + Compound of Example 4 (100 μM) | 2.3 |
| 4 | Insulin | 1 |
|   | Insulin + rosiglitazone (10 μM) | 6.3 |
|   | Insulin + Compound of Example 2 | 2 |
| 5 | Insulin | 1 |
|   | Insulin + rosiglitazone (10 μM) | 4 |
|   | Insulin + Compound of Example 8 | 1.8 |

Example 11

Streptozotocin-Induced Diabetes in Rats

Diabetes was induced in male Wistar rats by intraperitoneal (i.p.) injection of streptozotocin (STZ) (60 mg/kg) dissolved in 0.05 M citrate buffer, pH 4.6. Plasma glucose levels were estimated 48 hours after STZ administration. The mean levels of plasma glucose during the experiment were significantly higher in the STZ-diabetic group than in the untreated (control) group. The rats were divided into three groups (n=8 in each group): the first (control) group consisted of untreated animals, the second group had diabetic animals and the third and fourth groups consisted of diabetic animals treated with the test compounds (50 and 100 mg/kg respectively). Test compounds were administered p.o. for 8 days to STZ induced diabetic rats (180-200 g). Blood glucose was measured on day 0, 3 and 8 (Table 3).

TABLE 3

Blood glucose levels

| Group | Blood glucose (μmols/ml) | | |
|---|---|---|---|
|   | Day 0 | Day 3 | Day 8 |
| Control | 5.7 ± 1.09 | 5.6 ± 0.8 | 4.8 ± 2.0 |
| Diabetic | 17.2 ± 1.01 | 18.0 ± 0.9 | 18.9 ± 1.9 |
| Compound of Example 5 (50 mpk) | 16.8 ± 0.9 | 15.9 ± 3.0 | 14.1 ± 1.99 |
| Compound of Example 5 (100 mpk) | 17.0 ± 2.0 | 16.0 ± 1.09 | 13.0 ± 0.9 |

Percent reduction in blood glucose:
At 50 mpk=28%; At 100 mpk=31%.

Example 12 hPPAR γ/α Transactivation in Cell-Based Assay

The assay was designed as in references, J. Biol. Chem., 270(22), 12953-12956, 1995 and Diabetes, 47, 1841-1847, 1998, the disclosure of these two references are incorporated by reference for the teaching of the assay.

Cell based transcription assay was employed to identify hPPAR γ/α agonists. CV-1 cells were maintained in MEM (minimum essential medium) containing 10% FBS (fetal bovine serum). Cells were seeded at a density of 80,000 cells/well in a 24-well plate one day prior to transfection. CV-1 cells were transiently transfected with hPPAR γ/α using Lipofectamine 2000. Test compounds, or the full PPARγ agonist rosiglitazone (1 μM), or PPARα agonist Wy-14643 (20 μM), were added five hours after transfection. Receptor activation by ligands leads to activation of luciferase expression, which was measured after 15-16 h incubation. The cells were washed with PBS, lysed, and luciferase activity measured in a microplate luminometer. PPARγ and PPARα agonist potencies of test compounds were compared with reference agonists, Rosiglitazone and Wy-14643, respectively. Both compounds were synthesized in-house. Maximum activation with the reference agonists was defined as 100%. Receptor activation by test compounds is presented as percentage of maximum activation caused by the respective reference agonists in Table 4(a), Table 4(b) and Table 4(c).

TABLE 4(a)

hPPAR γ transactivation in cell-based assay

| Test Compound | PPARγ (Fold activation at 1 μM) |
|---|---|
| Rosiglitazone | 8.1 (100%) |
| Compound of Example 7 | 0.7 (9%) |

TABLE 4(b)

hPPAR α transactivation in cell-based assay

| Test Compound | PPARα (Fold activation at 20 μM) |
|---|---|
| Wy-14,643 | 3.2 (100%) |
| Compound of Example 7 | 1.5 (47%) |

TABLE 4(c)

hPPAR γ transactivation in cell-based assay

| Test Compound | PPARγ (Fold activation at 1 μM) |
|---|---|
| Rosiglitazone | 14.5 (100%) |
| Compound of Example 5 | 1.8 (12%) |

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A compound of formula (I),

[Structure of formula (I)]

wherein:
-------- (dotted line) represents an optional bond;
$R^1$ is:

[Structures showing various $R^1$ groups]

where:
$R^3$ and $R^4$ are, independently of each other:
hydrogen; hydroxyl; alkoxy; $C_1$-$C_4$ alkyl; amino; or aryl;
$R^5$, $R^6$ and $R^7$ are, independently of each other:
hydrogen; $C_1$-$C_4$ alkyl; or aryl;
n is 0, 1 or 2; and
the arrows indicate the point of attachment of $R^1$ group;
$R^2$ is:
mono or bicyclic heteroaryl, containing one nitrogen and optionally another heteroatom selected from nitrogen, sulphur or oxygen;
which may be unsubstituted or substituted with $R^8$, wherein $R^8$ is:
hydrogen; hydroxyl; alkoxy; $C_1$-$C_4$ alkyl; halogen; amino; or aryl; and
a stereoisomer, geometric isomer or pharmaceutically acceptable salt thereof.

2. The compound according to claim 1, wherein $R^1$ is:

[Structures showing $R^1$ groups]

where:
$R^3$ and $R^4$ are, independently of each other:
hydrogen; hydroxyl; alkoxy; $C_1$-$C_4$ alkyl; amino; or aryl;
$R^5$ and $R^6$ are, independently of each other:
hydrogen; $C_1$-$C_4$ alkyl; or aryl;
n is 0, 1 or 2;
the arrows indicate the point of attachment of $R^1$ group; and
a stereoisomer, geometric isomer or pharmaceutically acceptable salt thereof.

3. The compound according to claim 2, wherein:
$R^1$ is:

[Structures showing $R^1$ groups]

where:
$R^3$ and $R^4$ are, independently of each other:
hydroxyl or alkoxy;
$R^5$ is:
hydrogen; $C_1$-$C_4$ alkyl; or aryl;
n is 0, 1 or 2;
the arrows indicate the point of attachment of $R^1$ group; and
a stereoisomer, geometric isomer or pharmaceutically acceptable salt thereof.

4. The compound according to claim 3, wherein $R^1$ is:

[Structure showing $R^1$ group]

where:
$R^3$ and $R^4$ are, independently of each other:
hydroxyl or alkoxy;
n is 0, 1 or 2;
the arrow indicates the point of attachment of $R^1$ group; and
a stereoisomer, geometric isomer or pharmaceutically acceptable salt thereof.

5. The compound according to claim 1, wherein $R^1$ is:

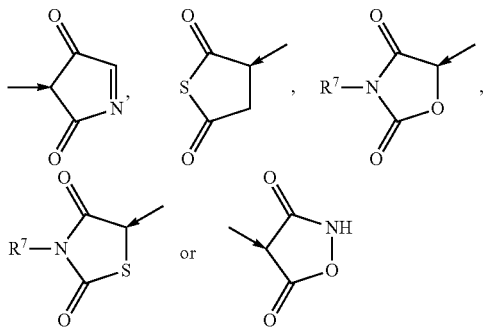

where:
$R^7$ is:
hydrogen; $C_1$-$C_4$ alkyl; or aryl;
the arrows indicate the point of attachment of $R^1$ group; and
a stereoisomer, geometric isomer or pharmaceutically acceptable salt thereof.

6. The compound according to claim 5, wherein $R^1$ is:

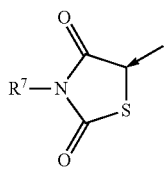

where:
$R^7$ is:
hydrogen or $C_1$-$C_4$ alkyl;
the arrow indicates the point of attachment of $R^1$ group; and
a stereoisomer, geometric isomer or pharmaceutically acceptable salt thereof.

7. A compound according to claim 1, wherein:
$R^2$ is heteroaryl selected from:

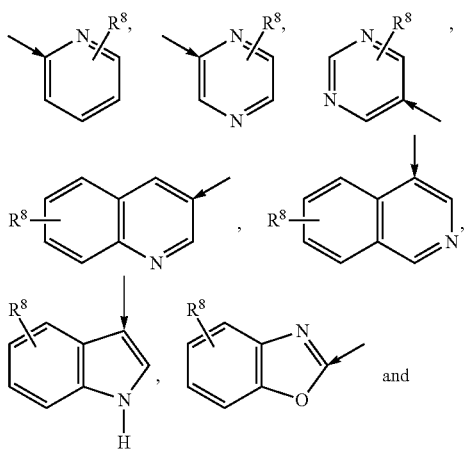

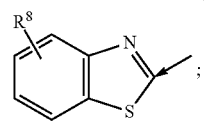

where:
$R^8$ is:
hydrogen; hydroxyl; alkoxy; $C_1$-$C_4$ alkyl; halogen; amino; or aryl;
the arrows indicate the point of attachment of $R^2$ group to the benzoxazepine core; and
a stereoisomer, geometric isomer, or pharmaceutically acceptable salt thereof.

8. The compound according to claim 7, wherein $R^2$ is heteroaryl selected from:

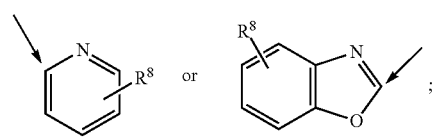

where:
$R^8$ is:
hydrogen; hydroxyl; alkoxy; $C_1$-$C_4$ alkyl; halogen; amino; or aryl;
the arrows indicate the point of attachment of $R^2$ group to the benzoxazepine core; and
a stereoisomer, geometric isomer or pharmaceutically acceptable salt thereof.

9. The compound according to claim 1, wherein $R^1$ is:

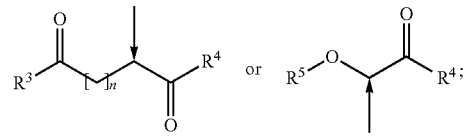

$R^3$ and $R^4$ are, independently of each other:
hydroxyl or alkoxy;
$R^5$ is:
hydrogen; $C_1$-$C_4$ alkyl; or aryl;
n is 0, 1 or 2;
$R^2$ is heteroaryl selected from:

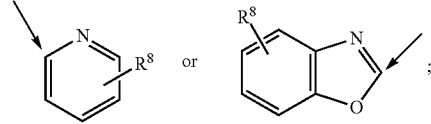

where:
$R^8$ is:
hydrogen; hydroxyl; alkoxy; $C_1$-$C_4$ alkyl; halogen; amino; or aryl;
the arrows indicate the point of attachment of $R^2$ group to the benzoxazepine core; and
a stereoisomer, geometric isomer or pharmaceutically acceptable salt thereof.

10. The compound according to claim 1, wherein R$^1$ is:

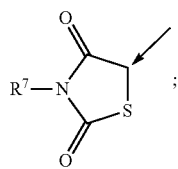

where:

R$_7$ is:

hydrogen or C$_1$-C$_4$ alkyl;

the arrow indicates the point of attachment of R$^1$ group;

R$^2$ is heteroaryl selected from:

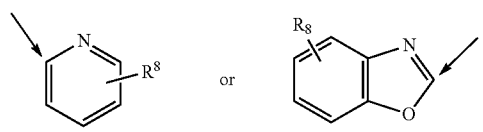

where:

R$^8$ is:

hydrogen; C$_1$-C$_4$ alkyl; or halogen;

the arrows indicate the point of attachment of R$^2$ group to the benzoxazepine core; and a stereoisomer, geometric isomer or pharmaceutically acceptable salt thereof.

11. The compound according to claim 1, wherein the optional double bond (--------) is absent.

12. The compound according to claim 1, wherein the compound is selected from:

2-(4-pyridin-2-yl-2,3,4,5-tetrahydro-benzo[f][1,4]oxazepin-7-ylmethyl)-malonic acid dimethyl ester, 2-(4-pyridin-2-yl-2,3,4,5-tetrahydro-benzo[f][1,4]oxazepin-7-yl)-methylene)-malonic acid dimethyl ester, 5-(4-pyridin-2-yl-2,3,4,5-tetrahydro-benzo[f][1,4]oxazepin-7-ylmethyl)-thiazolidine-2,4-dione, 5-(4-pyridin-2-yl-2,3,4,5-tetrahydro-benzo[f][1,4]oxazepin-7-ylmethylene)-thiazolidine-2,4-dione, 5-(4-benzooxazol-2-yl-2,3,4,5-tetrahydro-benzo[f][1,4]oxazepin-7-ylmethyl)-thiazolidine-2,4-dione, 5-(4-benzooxazol-2-yl-2,3,4,5-tetrahydro-benzo[f][1,4]oxazepin-7-ylmethylene)-thiazolidine-2,4-dione, 5-(4-pyridine-2-yl-2,3,4,5-tetrahydro-benzo[f][1,4]oxazepin-7-ylmethyl)-thiazolidine-2,4-dione maleate; or 5 -(4-pyridin-2-yl-2,3,4,5-tetrahydro-benzo[f][1,4]oxazepin-7-ylmethylene)-thiazolidine-2,4-dione maleate; or a stereoisomer, geometric isomer or pharmaceutically acceptable salt thereof.

13. A process for the preparation of a compound of formula (I) according to claim 1, or a pharmaceutically acceptable salt thereof,

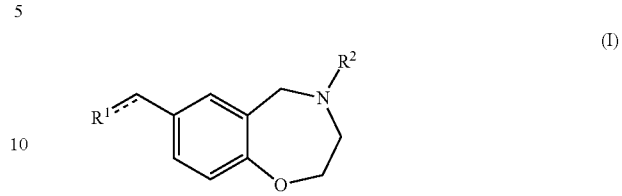

(I)

wherein:

-------- (dotted line) represents an optional bond; and

R$^1$ and R$^2$ are as defined in claim 1, which process comprises the steps of:

a) chloromethylation of compound of formula (2), wherein R$^2$ is as defined in claim 1, with formaldehyde in presence of hydrochloric acid and a Lewis acid at a temperature in the range of 10° C. to 50° C. for 24 to 72 hours to give compound of formula (3), wherein R$^2$ is as defined in claim 1;

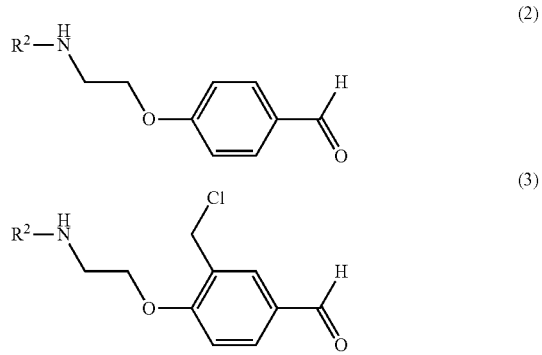

b) cyclisation of compound of formula (3), wherein R$^2$ is as defined in claim 1, in the presence of potassium iodide and/or potassium fluoride, optionally in the presence of a base selected from sodium carbonate, potassium carbonate and potassium bicarbonate, in DMF, dioxane or THF, at a temperature in the range of 50° C. to 150° C. from 0.5 to 5 hours to give compound of formula (II), wherein R$^2$ is as defined in claim 1;

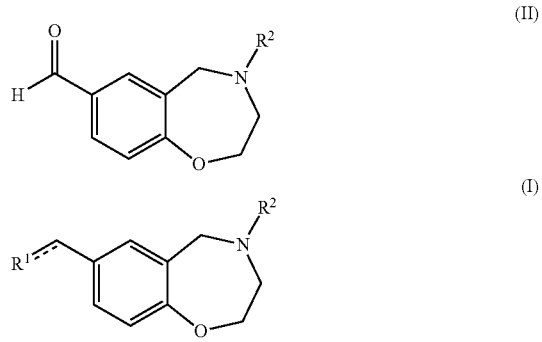

c) reaction of compound of formula (II) with R$^1$—H, wherein R$^1$ is as defined in claim 1, either (i) in the presence of a Lewis acid catalyst in a solvent selected from chloroform, carbon tetrachloride, tetrahydrofuran, ether and dioxane, or in a mixture of two or more of these solvents, in presence of pyridine, at a temperature in the range of 0° C. to ambient temperature, for 2 to 24 hours; or (ii) in the presence of piperidinium acetate in toluene, refluxed in a Dean Stark apparatus to give compound of formula (I), wherein $R^1$ and $R^2$ are as defined in claim 1 and the optional double bond is present;

d) optionally reducing the double bond of compound of formula (I) obtained in step (c) with Al-amalgam in a solvent selected from dioxane or 1,2-dimethoxyethane at a temperature in the range of –10° C. to 15° C. for 2 to 6 hours, or by catalytic hydrogenation, to give compound of formula (I), wherein $R^1$ and $R^2$ are as defined in claim 1 and ----- represents no bond;

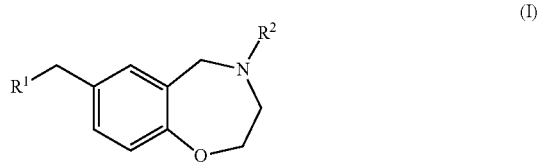

(I)

e) optionally converting compound of formula (I) wherein $R^1$ and $R^2$ are as defined in claim 1, into a pharmaceutically acceptable salt.

14. The process according to claim 13, wherein the Lewis acid is zinc chloride, ferric chloride or aluminium chloride.

15. The process according to claim 13, wherein catalytic hydrogenation is carried out in presence of gaseous hydrogen and a catalyst selected from Pd—C, Rh—C and Pt—C in a solvent selected from dioxane, acetic acid, ethyl acetate, methanol and ethanol, at a pressure between atmospheric pressure and 40 psi, at ambient temperature, for 6 to 24 hours.

16. A pharmaceutical composition, comprising a therapeutically effective amount of a compound of formula (I) according to claim 1, or a stereoisomer or pharmaceutically acceptable salt thereof, and a pharmaceutically acceptable carrier or diluent.

17. A method for the treatment of insulin resistance or conditions associated with insulin resistance, comprising administering to a human or non-human mammal in need thereof, a therapeutically effective amount of a compound of the formula (I), as claimed in claim 1, or a stereoisomer, geometric isomer, or pharmaceutically acceptable salt thereof, wherein the conditions associated with insulin resistance comprise type 2 diabetes mellitus, lipid and carbohydrate metabolism disorders, dyslipidemia, hyperinsulinemia, glucose intolerance, or obesity.

18. The method according to claim 17, wherein the condition associated with insulin resistance comprises type 2 diabetes mellitus.

* * * * *